United States Patent [19]

Matsuo et al.

[11] Patent Number: 4,740,612
[45] Date of Patent: Apr. 26, 1988

[54] PROCESS FOR PRODUCTION OF β-DIHALOGENOETHENYLCYCLOPROPANE DERIVATIVES

[75] Inventors: Takashi Matsuo, Saitama; Nobushige Itaya, Nishinomiya; Osamu Magara, Osaka, all of Japan

[73] Assignee: Sumitomo Chemical Company, Limited, Osaka, Japan

[21] Appl. No.: 825,966

[22] Filed: Feb. 5, 1986

Related U.S. Application Data

[63] Continuation of Ser. No. 512,951, Jul. 13, 1983, abandoned, which is a continuation of Ser. No. 653,613, Jan. 29, 1976, abandoned.

[30] Foreign Application Priority Data

Feb. 12, 1975 [JP] Japan ................... 50-18295
Feb. 12, 1975 [JP] Japan ................... 50-18296
Feb. 12, 1975 [JP] Japan ................... 50-18297
Feb. 12, 1975 [JP] Japan ................... 50-18298

[51] Int. Cl.⁴ .......................... C07C 69/743
[52] U.S. Cl. ................... 560/124; 560/174; 560/192; 562/506; 568/303; 568/348; 568/393
[58] Field of Search ............. 560/124, 174; 562/506; 568/303, 348, 393

[56] References Cited

U.S. PATENT DOCUMENTS

| | | | |
|---|---|---|---|
| 2,554,533 | 5/1951 | Ladd ................. | 260/487 |
| 2,561,516 | 7/1951 | Ladd ................. | 260/487 |
| 3,122,587 | 2/1964 | Stansbury ........... | 260/514 |
| 3,310,589 | 3/1967 | Ketley .............. | 260/487 |
| 3,354,196 | 11/1967 | Julia ............... | 260/468 |
| 3,651,019 | 3/1972 | Asscher ............. | 570/257 |
| 3,652,652 | 3/1972 | Julia ............... | 260/468 |
| 3,862,978 | 1/1975 | Decker .............. | 260/487 |
| 4,214,097 | 7/1980 | Kondo ............... | 560/213 |

FOREIGN PATENT DOCUMENTS

920855  3/1963  United Kingdom ........ 570/257

OTHER PUBLICATIONS

Fuson, Chem. Rev., 15, pp. 275–309 (1934).
Durand-Dran., Ann. Chim., 13, pp. 43–46, & 55–62 (1959).
Matsui, Abst. of Papers of 31st Autumn Annual Meeting of Chem. Soc. of Jap., p. 58 (9/25/74).
Sandler, "Organic Functional Group Preparations", vol. II, pp. 83–94, 113–118, 247–257 & 265–267 (1971).
Adams, "Organic Reactions", vol. 13, pp. 91–101 & 147–149.
Asscher, J. Chem. Soc., pp. 2261–2264 (1961).
Roberts, "Basic Principles of Organic Chemistry", pp. 477–478 (1964).
Allinger, "Organic Chemistry", pp. 550–552 (1971).

*Primary Examiner*—Michael L. Shippen
*Attorney, Agent, or Firm*—Stevens, Davis, Miller & Mosher

[57] ABSTRACT

A novel process for producing a β-dihalogenoethenylcyclopropane derivative of the formula,

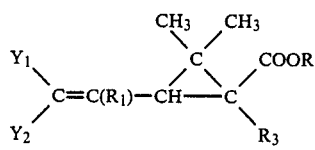

wherein $R_1$ is a hydrogen atom or an alkyl group, $R_3$ is a hydrogen atom, lower alkyl, acyl, carboxyl or alkoxycarbonyl group and R is a hydrogen atom or a lower alkyl group and each of $Y_1$ and $Y_2$ is a fluorine, chlorine or bromine atom respectively, which is an acidic moiety of the useful synthetic insecticides of the pyrethrin type, which process comprises a combination of a series of sequential steps starting from alkyl 3-butenyl ketone derivative of the formula (I), which may be shown according to the following reaction scheme:

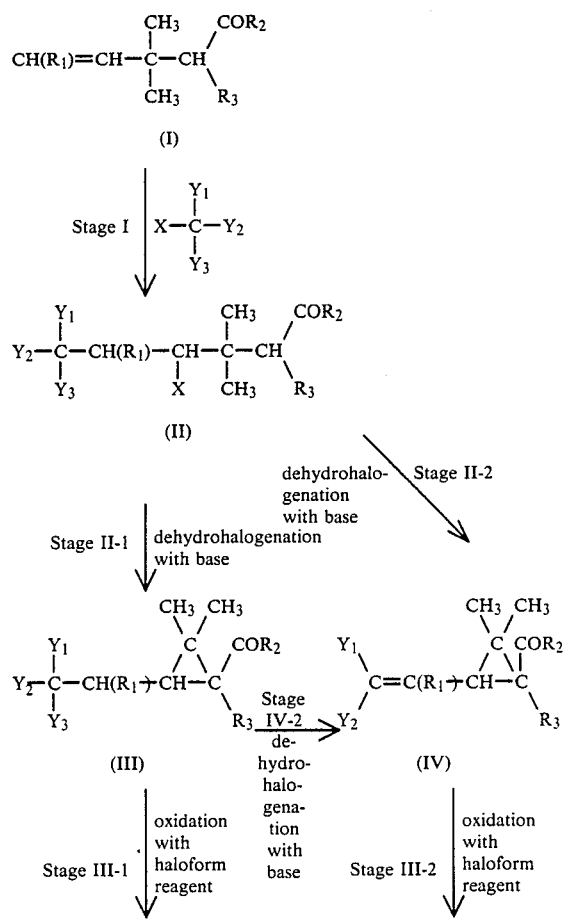

(Abstract continued on next page.)

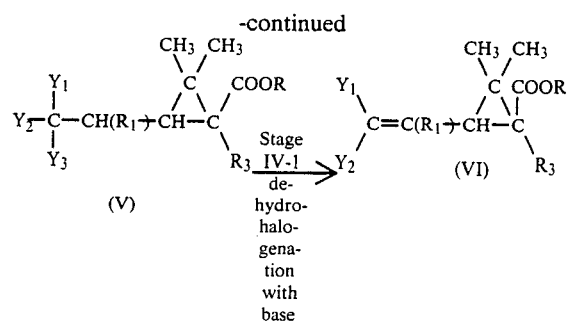
According to this process, objective compound of the formula (VI) having any cis/trans ratio can be produced by selecting the reaction condition of the Stages II-1, II-2, and IV-2.
12 Claims, No Drawings

PROCESS FOR PRODUCTION OF β-DIHALOGENOETHENYLCYCLOPROPANE DERIVATIVES

This application is a continuation of application Ser. No. 512,951, filed July 13, 1983, which in turn is a continuation of application Ser. No. 653,613, filed Jan. 29, 1976, now abandoned.

The present invention relates to a process for producing an intermediate compound and more particularly to a process for producing an acidic moiety of the useful synthetic insecticides of the pyrethrin type.

The present inventors have studied on the improvement of the process for the production of a β-dihalogenoethenylcyclopropanecarboxylic acid derivative which is the acidic moiety of the useful insecticides disclosed in the Japanese Laid-Open No. 47531/1974, and found a novel and advantageous process consisting of a combination of steps, by which β-dihalogenoethenylcyclopropane derivatives can be produced in good yield.

Accordingly, an object of the present invention is to provide a process for producing a β-dihalogenoethenylcyclopropanecarboxylic acid derivative which is an acidic moiety of the synthetic insecticides of the pyrethrin type in good yield.

Another object is to provide a novel intermediate compound for producing a β-dihalogenoethenylcyclopropanecarboxylic acid derivative.

The process of the present invention consists of a combination of a series of steps starting from alkyl 3-butenyl ketone derivative of the formula (I), which may be shown according to the following scheme:

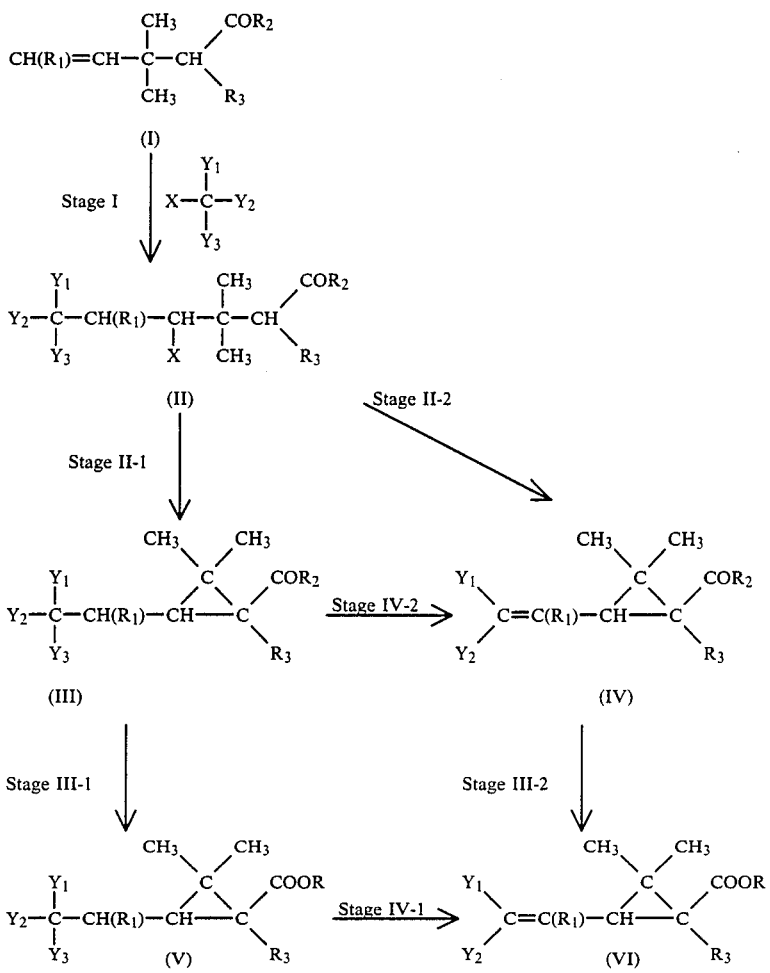

Thus, the present invention provides a process for the production of a β-dihalogenoethenylcyclopropanecarboxylic acid derivative of the formula (VI), which comprises a series of sequential steps of reacting an alkyl 3-butenyl ketone derivative of the formula (I) with a tetrahalogenomethane of the formula

to form an alkyl 3,5,5,5-tetrahalogenopentyl ketone derivative of the formula (II), reacting the resulting 3,5,5,5-tetrahalogenopentyl ketone derivative of the formula (II) with a base to form an alkyl cyclopropyl ketone derivative of the formula (III) or (IV) depending on the reaction condition, oxidizing the resulting alkyl cyclopropyl ketone derivative of the formula (III) or (IV) to form a cyclopropanecarboxylic acid derivative of the formula (V) or (VI) and then reacting the resulting β-trihalogenoethylcyclopropane derivative of the formula (V) with a base to form a β-dihalogenoethenyl-cyclopropanecarboxylic acid derivative of the formula (VI).

In similar way, a ketone derivative of the formula (III) can be reacted with base to form a ketone derivative of the formula (IV).

The first step of the process of the present invention is a reaction of an alkyl 3-butenyl ketone derivative of the formula (I),

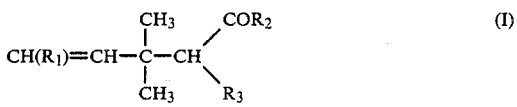

wherein $R_1$ is a hydrogen atom or an alkyl group, $R_2$ is an alkyl group and $R_3$ is a hydrogen atom, a lower alkyl, acyl or alkoxycarbonyl group, with a tetrahalogenomethane of the formula,

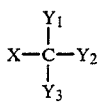

wherein X is a chlorine or bromine atom and each of $Y_1$, $Y_2$ and $Y_3$ is a fluorine, chlorine or bromine atom respectively, provided that when X is a chlorine atom each of $Y_1$, $Y_2$ and $Y_3$ is fluorine or chlorine atom to form an alkyl 3,5,5,5-tetrahalogenopentyl ketone derivative of the formula (II),

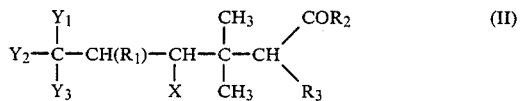

wherein $R_1$, $R_2$, $R_3$, X, $Y_1$, $Y_2$ and $Y_3$ are as defined above.

The alkyl 3-butenyl ketone derivative of the formula (I) of this invention includes well-known compounds which are disclosed in literatures, and can be prepared by the methods disclosed in literatures.

For example, methyl 2,2-dimethyl-3-butenyl ketone of the formula,

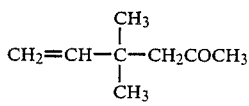

may be easily prepared by the reaction of the prenyl alcohol of the formula,

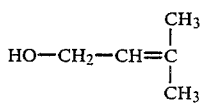

with ethyl enol ether of acetoacetic acid ethyl ester of the formula,

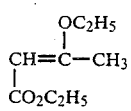

according to the method of K. Brack et al. (Helv. Chim. Acta, 34, 2005 (1951)). In carrying out the Claisen rearrangement the reaction may be conducted by using an organic base such as, for example, quinoline.

In this invention, the alkyl group which is meant by $R_1$ and $R_2$ is for example a lower alkyl group, and the alkoxycarbonyl group which is meant by $R_3$ is for example a methoxycarbonyl, ethoxycarbonyl or t-butoxycarbonyl group.

The reaction of the first step of the present invention is a radial reaction. The reaction of this step needs no catalyst when it is carried out at high temperatures or under irradiation with light. But it can be carried out more smoothly by adding suitable radical initiators or catalysts, if necessary. The radical initiator includes for example benzoylperoxide, azobisisobutyronitrile or the like.

As the catalyst, a combination of cuprous, cupric, ferrous or ferric salts with suitable reducing agents or transition metal complex may be used. The typical reducing agent includes monoethanolamine, diethanolamine, triethanolamine, benzoin and the like. However, the reducing agent of this invention is not limited to those compounds.

The catalyst or reducing agent may be added in the course of the reaction depending upon the progress of the reaction.

The reaction may be carried out, if necessary, in the presence of an organic solvent such as t-butyl alcohol, t-amyl alcohol, isopropyl alcohol, acetonitrile, dimethylformamide, dimethylsulfoxide and the like. The reaction temperature is generally from 30° C. to 200° C., but the temperature of from 60° C. to 150° C. is particularly preferable. The reaction pressure is not particularly limited, but in most cases it is an atmospheric pressure or within a range of 1 to 50 atmospheres. The reaction period of time depends upon the reaction temperature, pressure and the kind and amount of catalysts, but generally it is within a range of 30 minutes to 48 hours. The alkyl 3,5,5,5-tetrahalogenopentyl ketone derivative of the formula (II) obtained by the reaction of the first step of this invention is a novel compound which has not been disclosed in literatures.

The second step of the process of the present invention is a base treatment of 3,5,5,5-tetrahalogenopentyl ketone derivative of the formula (II),

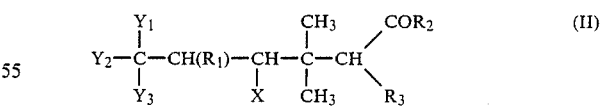

wherein $R_1$, $R_2$, $R_3$, X, $Y_1$, $Y_2$ and $Y_3$ are as defined above to form a cyclopropane derivative of the formula (III) or (IV),

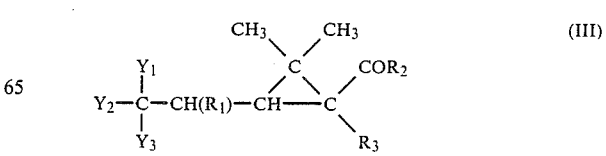

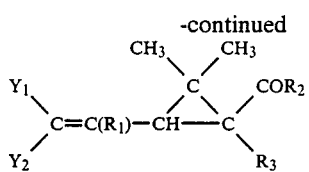

wherein $R_1$, $R_2$, $Y_1$, $Y_2$ and $Y_3$ are as defined above, and $R_3$ is a hydrogen atom, lower alkyl, acyl, carboxyl or alkoxycarbonyl group.

The reaction of the second step of the present invention is a dehydrohalogenation reaction. Depending upon the reaction condition, there are a case where hydrogen halogenide, HX in which X is as defined above, is removed and another case where hydrogen halogenide, $HY_1$, $HY_2$ or $HY_3$ in which $Y_1$, $Y_2$ or $Y_3$ is as defined above, is further removed at the same time.

As the result of the formation of cyclopropane ring by the dehydrohalogenation reaction cis and trans isomers are formed. And by selecting the reaction condition a product having wide range of cis/trans ratio of from 1:9 to 9:1 can be obtained. A cis/trans ratio of 9:1 can be considered cis-rich while a ratio of 1:9 can be considered trans-rich. Therefore in order to achieve the object of this invention, it is necessary to select the proper reaction condition.

The base which is used in the reaction of the second step of this invention includes alkali hydroxides such as sodium hydroxide, potassium hydroxide, calcium hydroxide and the like, and alkali metal alcoholates such as sodium methoxide, sodium ethoxide, sodium t-amylate, potassium t-butoxide and the like. However the base of this invention is not of course limited to those compounds.

In the reaction of the second step of this invention, it is desirable if necessary to carry out the reaction in water, organic solvents or in a mixed solvent of water with an alcohol having 8 or less carbon atoms. The organic solvent includes alcohols having 8 or less carbon atoms such as for example methanol, ethanol, propanols, butanols, ethers such as for example tetrahydrofuran, dioxane, diethyl ether, aromatic hydrocarbons such as for example benzene, toluene, xylene and the like.

The reaction temperature of the second step is not particularly limited, but it is generally from −20° C. to 120° C.

In general, if the reaction is conducted in a lower alcohol such as methanol at a lower temperature, for example, from −20° C. to 25° C., cis-rich isomer of the formula (III) is obtained and when the reaction is conducted at a higher temperature trans-rich isomer of the formula (III) and/or formula (IV) is obtained, but the kind of the reaction product and cis/trans ratio are also varied depending upon other reaction condition such as for example the kind of base to be employed.

The reaction period of time depends upon the reaction temperature and the kind of base, but the reaction usually comes to an end in 30 minutes to 10 hours.

The reaction of the second step of this invention produces the alkyl cyclopropyl ketone derivative of the formula (III) or (IV) in a very high yield.

In this invention, when the group $R_3$ in the formula (II) is an alkoxycarbonyl group, it sometimes occurs that the reaction product of the formula (III) or (IV) wherein $R_3$ is a carboxyl group is obtained depending upon the reaction condition, particularly when the reaction system contains water and/or alkali hydroxide.

The alkyl cyclopropyl ketone derivative of the formulas (III) and (IV) which are obtained by the reaction of the second step of this invention are novel compounds which have not been disclosed in literatures.

The third step of the process of this invention is an oxidation of the alkyl cyclopropyl ketone of the formula (III) or (IV),

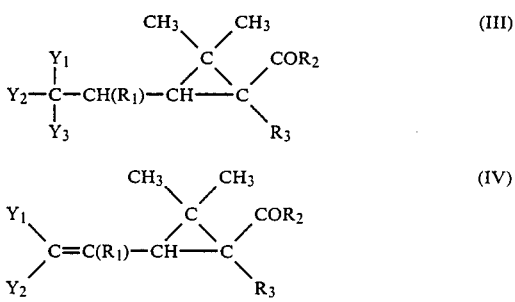

wherein $R_1$, $R_2$, $R_3$, $Y_1$, $Y_2$ and $Y_3$ are defined above to form a carboxylic acid derivative of the formula (V) or (VI),

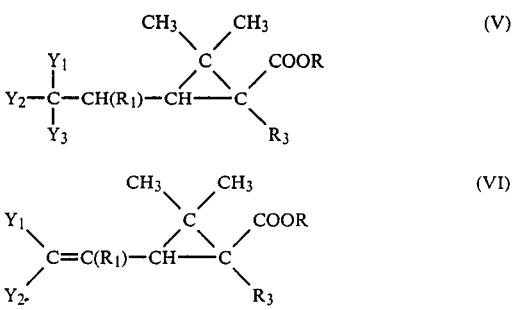

wherein $R_1$, $R_3$, $Y_1$, $Y_2$ and $Y_3$ are as defined above and R is a hydrogen atom or a lower alkyl group. In this reaction, an oxidation of the compound of the formula (III) forms the compound of the formula (V) and oxidation of the compound of the formula (IV) forms the compound of the formula (VI), respectively.

The oxidizing agent which is used in the third step of the present invention refers to those which can convert the group —$COR_2$ (in which $R_2$ is as defined above) to a carboxyl group or alkoxycarbonyl group without affecting other groups in the formulas (III) and (IV). Particularly when the compound of the formula (IV) is employed, attention must be given not to affect the double bond between the two carbon atoms. From the object of this invention, it is included in the scope of this invention that the carboxyl or alkoxycarbonyl group which is meant by $R_3$ is converted to a hydrogen atom or carboxyl group, respectively, in the course of reaction.

The most preferred method of the third step of this invention is to react the methyl cyclopropyl ketone derivative, which is a compound of formula (III) or (IV) wherein $R_2$ is a methyl group, with a haloform reagent of the formula, MOX', in which M is a sodium, potassium or calcium atom and X' is a chlorine, bromine or iodine atom. The haloform reagent used includes sodium hypochlorite, potassium hypochlorite, calcium hypochlorite, sodium hypobromite, potassium hypobromite, calcium, hypobromite and the like. Further, the reaction can also be carried out by introducing a halogen into an aqueous alkali hydroxide solution of a starting material.

If the reaction is conducted in the presence of a lower alcohol, it is advantageous to add a halogen to the reaction mixture in the course of the reaction to generate a hypohalite in the reaction system. In this case the reaction proceeds immediately. The reaction product formed is varied depending upon the reaction condition and the composition of the solvent used, and together with the objective carboxylic acid is formed an ester of the lower alcohol employed, which is easily resolved to the carboxylic acid by subjecting hydrolysis with an alkali. Additionally, a mixture of iodine and potassium iodide can also be used. The reaction temperature is not particularly limited, but preferably $-20°$ C. to $70°$ C. Water is generally used as a solvent, but if necessary polar solvents may be added as a reaction auxiliary in order to allow the reaction to proceed more smoothly. The reaction period of time depends upon the reagent used and reaction temperature, but in most cases the end point of reaction is reached in 2 to 24 hours with a very high yield.

The compounds of formulas (III), (IV), (V) and (VI) includes geometrical and optical isomers with respect to the three-membered ring, all of which are of course included in this invention.

The cyclopropanecarboxylic acid derivative of the formula (V) obtained by the reaction of the third step of this invention is a novel compound which has not been disclosed in literatures.

Of the cyclopropanecarboxylic acid derivatives of the formula (VI) which are obtained by the reaction of the third step of this invention, the compounds wherein $R_3$ is a hydrogen atom are used as such as the intermediate for insecticidal compounds which are disclosed in the above-mentioned Laid-Open No. 47531/1974. Other derivatives are used for the same purpose after they are subjected to decarboxylation or removal of alkoxycarbonyl group.

The fourth step of this invention is a base. treatment of a $\beta$-trihalogenoethylcyclopropane derivative of the formula (V) or (III) to form a $\beta$-dihalogenoethenylcyclopropane derivative of the formula (VI) or (IV), respectively.

The base employed in the fourth step of this invention includes alkali hydroxides such as sodium hydroxide, potassium hydroxide, calcium hydroxide and the like, and alkali metal alcoholates such as sodium methoxide, sodium ethoxide, sodium t-amyloxide, potassium t-butoxide and the like. However, the base is not limited to those compounds.

In the reaction of the fourth step of this invention, the base is used in an amount at least enough to remove hydrogen halogenide from the $\beta$-trihalogenoethylcyclopropane derivative of formula (V) or (III).

The reaction of the fourth step of this invention may be carried out in water or in an organic solvent such as alcohols, ethers e.g. tetrahydrofuran, diethyl ether, aromatic hydrocarbons e.g. benzene, toluene, xylene and the like, or if necessary in a mixture of these solvents.

The reaction temperature of the fourth step of this invention is a usual one which is not particularly limited, but in general the reaction is advantageously carried out in the vicinity of the boiling point of solvents used.

The reaction period of time of this invention depends upon the starting material, base, solvent or reaction temperature, but is generally from 30 minutes to 10 hours.

In the fourth step of this invention, when the group $R_3$ in the formula (V) or (III) is an alkoxycarbonyl group, it sometimes occurs that the reaction product of the formula (VI) or (IV) wherein $R_3$ is a carboxyl group is obtained depending upon the reaction conditions, particularly when the reaction system contains water and/or alkali hydroxide.

In the series of sequential steps of the process of the present invention, a base is employed as the same reaction reagent in each steps of from second to fourth steps, and accordingly, the each step of the series of the reaction can be conducted successively in the same reaction vessel. And the cis/trans ratio of the objective product formed may be varied by selecting the reaction condition or by selecting the reaction course in the series of the reaction steps. For example, if the reaction of the second step is conducted using a caustic alkali in the presence of a lower alcohol at a lower temperature cis-rich isomer of the formula (III) (e.g. $R_1=H$, $R_2=CH_3$, $R_3=H$) can be obtained which can be converted to cis-rich isomer of the formula (V) and then converted to cis-rich isomer of the formula (VI) through the reactions of the third and fourth steps.

On the other hand, the compound of the formula (III) may be reacted with caustic alkali to subject to a cis-trans isomerization reaction. In this case, if the isomerization is conducted under a severe condition, almost all of the compound is converted to trans isomer and at the same time, the dehydrohalogenation reaction, which is the reaction of the fourth step of the present invention, is occurred and the trans-rich isomer of the formula (IV) (e.g. $R_1=H$, $R_2=CH_3$, $R_3=H$) can be obtaind, which can be converted to the trans-rich isomer of the formula (VI) according to the reaction of the third step of the present invention.

Accordingly, objective compound having any cis/trans ratio ranging from cis-rich to trans-rich may be obtained by selecting the reaction conditions. In the above reaction, if the reaction is conducted using water as a reaction medium, a phase transfer catalyst may be employed as the reaction auxiliary agent for the purpose of making the reaction proceed more smoothly.

The present invention will be illustrated in more details with reference to the following examples, but it is not intended to limit this invention thereto.

STAGE I EXAMPLE 1

In 50 ml of t-amyl alcohol were dissolved 4.1 g of 4,4-dimethyl-5-hexene-2-one and then 0.1 g of cuprous chloride, 0.1 g of cupric chloride (dihydrate), 1 g of monoethanolamine and 15 g of carbon tetrachloride were added to the resulting solution. The mixture was refluxed for 12 hours. After removing the solvent under reduced pressure, 50 ml of water and 50 ml of benzene were added thereto and the mixture was shaken. The benzene layer was washed with 20 ml of an aqueous sodium chloride solution and dried over anhydrous magnesium sulfate. After removing the benzene under reduced pressure, vacuum distillation was carried out to obtain 4.8 g of 4,4-dimethyl-5,7,7,7-tetrachloroheptane-2-one as a pale yellow oily matter.

Boiling point: 110° C.–115° C./1 mmHg
Refractive index: 1.4970 (19.5° C.)
Yield: 52.7%

STAGE I EXAMPLE 2

In 15 g of carbon tetrachloride were dissolved 5.0 g of 3-ethoxycarbonyl-4,4-dimethyl-5-hexene-2-one and 0.3 g of benzoylperoxide was added to the resulting solution. The mixture was reacted at 120° C. for 3 hours in an autoclave.

The reaction solution was washed with an aqueous sodium sulfite solution and then the carbon tetrachloride was removed under reduced pressure. Vacuum distillation was carried out to obtain 8.4 g of 3-ethoxycarbonyl-4,4-dimethyl-5,7,7,7-tetrachloroheptane-2-one.

Boiling point: 120° C.–130° C./0.7 mmHg
Refractive index: 1.5018 (19.5° C.)
Yield: 94.5%

STAGE I EXAMPLE 3

Into a refluxing mixture of 52 g of 4,4-dimethyl-5-hexene-2-one (purity 89.0%), 127 g of carbon tetrachloride, 500 mg of cuprous chloride, 20 mg of cupric chloride (dihydrate) and 250 ml of t-amyl alcohol was added dropwise over 2 hours a solution obtained by dissolving 50.4 g of monoethanolamine, 300 mg of cuprous chloride and 10 mg of cupric chloride (dihydrate) in t-amyl alcohol to make the total 100 ml. After the reaction was over, a lower boiling point part was removed, the residue was diluted with water, extracted with ether, and after ether was removed from the ether layer, was subjected to a vacuum distillation to obtain 88.5 g of 4,4-dimethyl-5,7,7,7-tetrachloroheptane-2-one, b.p. 90°–100° C./0.4 mmHg, purity 91.6%, yield 78.8%.

STAGE I EXAMPLE 4

In similar way to that in Stage I Example 3 except that 274 g of carbon tetrabromide was used in place of 127 g of carbon tetrachloride, 137.7 g of 4,4-dimethyl-5,7,7,7-tetrabromoheptane-2-one, b.p. 120°–140° C./0.4 mmHg, purity 89.2%, yield 73.0%, was obtained.

STAGE I EXAMPLE 5

A mixture of 10.1 g of 4,4-dimethyl-5-hexene-2-one, 48 g of trichlorobromomethane and 50 mg of α,α'-azobis-iso-butyronitrile (hereinafter referred to as AIBN) was refluxed and further after 1 hour and 3 hours 50 mg each of AIBN was added under reflux. And after the mixture was refluxed for total 4 hours the same treatment as that in the Example 3 was conducted to obtain 3.1 g of the starting material and 13.7 g of 4,4-dimethyl-5-bromo-7,7,7-trichloroheptane-2-one, b.p. 95°–105° C./0.4 mmHg, purity 89.0%, yield 67.7%.

STAGE II-1 EXAMPLE 1

To 3.4 g of a 50% aqueous caustic soda solution were added 3.0 g of 4,4-dimethyl-5,7,7,7-tetrachloroheptane-2-one and the mixture was stirred at 100° C. for 3 hours. Thereafter 30 ml of benzene and 20 ml of water were added to the reaction mixture and the mixture was shaken. The benzene layer was washed with 20 ml of water and the benzene was removed using an evaporator. Vacuum distillation was carried out to obtain 2.3 g of the objective 2,2-dimethyl-3-cis,trans-(2',2',2'-trichloroethyl)-cyclopropyl methyl ketone as a colorless transparent oil.

Boiling point: 69.0° C.–74.0° C./0.4 mmHg
Refractive index: 1.4912 (21.0° C.)
Yield: 88.0%

STAGE II-1 EXAMPLE 2

To 3.0 g of a 50% aqueous caustic soda solution were added 2.5 g of 3-ethoxycarbonyl-4,4-dimethyl-5,7,7,7-tetrachloroheptane-2-one and the mixture was stirred at 50° C. for 5 hours.

To the reaction mixture were added 30 ml of benzene and 20 ml of water and the mixture was shaken to remove the neutral portion. The aqueous layer was made acidic to pH 1 with a 10% aqueous hydrochloric acid and extracted with 30 ml of benzene. The benzene layer was washed with 20 ml of a saturated aqueous sodium chloride solution and freed of the benzene using an evaporator. Vacuum distillation was carried out to obtain 1.48 g of the objective 1-hydroxycarbonyl-2,2-dimethyl-3-cis,trans-(2',2',2'-trichloroethyl)-cyclopropyl methyl ketone as a pale yellow oil.

Boiling point: 110° C.–125° C./0.2 mmHg
Refractive index: 1.5683 (21.0° C.)
Yield: 72.5%

STAGE II-1 EXAMPLE 3

Fifty six grams of 4,4-dimethyl-5,7,7,7-tetrachloroheptane-2-one (purity 91.6%) was dissolved in 160 ml of methanol and cooled to 0° C. Eighty milliliters of a methanol solution containing 9.6 g of sodium hydroxide was added dropwise thereto at 0° C. over 30 minutes, and then the stirring was continued for 1 hour at 0°–5° C., then the reaction mixture was diluted with water, neutralized with hydrochloric acid and extracted with ether. Upon vacuum distillation, 44.2 g of 2,2-dimethyl-3-cis,trans-(2',2',2'-trichloroethyl)-cyclopropyl methyl ketone, b.p. 78°–86° C./0.6 mmHg, cis/trans ratio 91.5/8.5, purity 99.6%, was obtained.

STAGE III-1 EXAMPLE 1

To a 50-ml four-necked flask were added 2.3 g of (±)-2,2-dimethyl-3-cis,trans-(2',2',2'-trichloroethyl)-cyclopropyl methyl ketone and then 15 g of a 10% aqueous sodium hypochlorite solution were added dropwise thereto at 0° C. to 5° C. The mixture was stirred for 2 hours at 0° C. to 5° C. and then for 12 hours at 20° C. to 25° C. The reaction mixture was extracted with 20 ml of benzene to remove unreacted materials and the aqueous layer was made acidic to pH 1 with a 10% aqueous hydrochloric acid. After the aqueous layer was extracted with 30 ml of benzene, the benzene layer was washed with 20 ml of water and the benzene was removed using an evaporator. Vacuum distillation was carried out to obtain 1.85 g of the objective (±)-2,2-dimethyl-3-cis,trans-(2',2',2'-trichloroethyl)-cyclopropane-1-carboxylic acid as a colorless transparent oil.

Boiling point: 120° C.–130° C./0.4 mmHg
Refractive index: 1.5020 (21° C.)
Yield: 80.0%

STAGE III-1 EXAMPLE 2

To a 50-ml four-necked flask were added 3.5 g of (±)-1-ethoxycarbonyl-2,2-dimethyl-3-cis,trans-(2',2',2'-trichloroethyl)-cyclopropyl methyl ketone, and then 20 g of a 10% aqueous sodium hypochlorite solution were added dropwise thereto at 0° C. to 5° C. The mixture was stirred for 2 hours at 0° C. to 5° C. and then for 15 hours at 20° C. to 25° C. The reaction mixture was extracted with 20 ml of benzene to remove unreacted materials and the aqueous layer was made acidic to pH 1 with a 10% aqueous hydrochloric acid. After the aqueous layer was extracted with 30 ml of benzene, the benzene layer was washed with 20 ml of water and the benzene was removed under reduced pressure. Vacuum distillation was carried out to obtain 1.9 g of the objective (±)-1-ethoxycarbonyl-2,2-dimethyl-3-cis,trans-(2',2',2'-trichloroethyl)-cyclopropane-1-carboxylic acid as a pale yellow oil.

Boiling point: 140° C.-145° C./0.1 mmHg
Refractive index: 1.5163 (21° C.)
Yield: 53.9%

STAGE III-1 EXAMPLE 3

To 250 ml of methanol solution containing 36 g of sodium hydroxide were added 26.8 g of 2,2-dimethyl-3-(2',2',2'-trichloroethyl)-cyclopropyl methyl ketone (purity: 97.9%, cis/trans ratio: 91.5/8.5) under cooling with ice, and then 27.6 g of chlorine gas were absorbed from the surface of the solution for 100 minutes and stirred for 30 minutes. Then 25.2 g of sodium sulfite (7 hydrate) and 200 ml of water were added and the mixture was stirred for 30 minutes to decompose excess hypochlorite. Then the reaction mixture was made acidic with conc. hydrochloric acid. After separating lower organic layer deposited, water layer was subjected to extraction with ether, and the ether layer was mixed with the separated organic layer and washed with sodium bicarbonate aqueous solution and a saturated sodium chloride aqueous solution. After distilling off the ether, vacuum distillation was carried out to obtain 8.3 g of methyl 2,2-dimethyl-3-(2',2',2'-trichloroethyl)-cyclopropanecarboxylate, b.p. 77°-86° C./0.4 mmHg, cis/trans ratio 88/12, purity 87.8%, yield 26.3% and 15 g of 2,2-dimethyl-3-(2',2',2'-trichloroethyl)-cyclopropanecarboxylic acid, b.p. 104°-120° C./0.4 mmHg, cis/trans ratio 82.8/17.2, purity 91.8%, yield 52.0%. Further, the sodium bicarbonate aqueous wash solution was acidified to obtain 1.4 g of 2,2-dimethyl-3-(2',2',2'-trichloroethyl)-cyclopropanecarboxylic acid.

STAGE III-2 EXAMPLE 1

Three grams (14.5 mmol) of 2,2-dimethyl-3-(2',2'-dichlorovinyl)-cyclopropyl methyl ketone (cis/trans=1/7.14) was dissolved in 100 ml of a methanol solution containing 5.2 g (130 mmol) of sodium hydroxide and 10.4 g of bromine was added dropwise thereto at a temperature of from 5° to 8° C. under stirring, while heat generation was observed. By gas chromatography analysis of the reaction mixture after the dropwise addition it was found that the starting material was already disappeared and that cis,trans methyl 2,2-dimethyl-3-(2',2'-dichlorovinyl)-cyclopropanecarboxylate was formed. To the reaction mixture was added 24.6 g of sodium sulfite (7 hydrate) to decompose excess amount of sodium hypobromite and the mixture was made acidic with hydrochloric acid and extracted with ether, and then concentrated and distilled to obtain 2.70 g of main fraction, b.p. 64°-67° C./0.2 mmHg and 0.27 g of distillation residue. All of the main fraction was methyl 2,2-dimethyl-3-(2',2'-dichlorovinyl)-cyclopropanecarboxylate consisting of 11.8% of cis isomer and 88.2% of trans isomer. And the distillation residue was 2,2-dimethyl-3-(2',2'-dichlorovinyl)-cyclopropanecarboxylic acid.

STAGE III-2 EXAMPLE 2

In similar way to that in Stage III-2 Example 1 except that chlorine gas was introduced into the reaction mixture in place of dropwise addition of bromine, the reaction was conducted. Result of the gas chromatography analysis immediately after the introduction of chlorine gas was almost the same as in the case of bromine.

STAGE III-2 EXAMPLE 3

Three grams (14.5 mmol) of 2,2-dimethyl-3-(2',2'-dichlorovinyl)-cyclopropyl methyl ketone was dissolved in 80 ml of a methanol solution containing 13.9 g (348 mmol) of sodium hydroxide and 4.87 g (68.6 mmol) of chlorine gas was introduced thereto under stirring. Heat generation was observed in some degree but the temperature was maintained at 7°-11° C. Then 12.7 g of sodium sulfite (7 hydrate) and 80 ml of water were added thereto and the mixture was stirred for 30 minutes at room temperature and then heated at 50° C. for 4 hours. Then the reaction mixture was made acidic with conc. hydrochloric acid under cooling to deposit crystals, which was separated by filtration, washed with water and then dried. The filtrate was extracted with ether, and the ether layer was washed with a saturated sodium bicarbonate aqueous solution and a sodium chloride aqueous solution to obtain neutral part.

Yield: acid (crystals), 2.67 g; neutral part, 0.1 g.
The crystals were 2,2-dimethyl-3-(2',2'-dichlorovinyl)-cyclopropanecarboxylic acid (cis/trans=8.1/91.9) and the neutral part was methyl 2,2-dimethyl-3-(2',2'-dichlorovinyl)-cyclopropanecarboxylate.

Stage IV-1 EXAMPLE 1

To a 20 ml eggplant shape flask were added 3.0 g of (±)-2,2-dimethyl-3-cis,trans-(2',2',2'-trichloroethyl)-cyclopropane-1-carboxylic acid and then 10 g of a 10% aqueous caustic soda solution were added dropwise thereto at room temperature. After refluxing for 5 hours, the reaction mixture was made acidic to pH 1 with a 10% aqueous hydrochloric acid and extracted with 50 ml of benzene. The benzene layer was washed with 20 ml of an aqueous sodium chloride solution and dried over anhydrous magnesium sulfate. After removing the benzene under reduced pressure, vacuum distillation was carried out to obtain 2.4 g of the objective (±)-2,2-dimethyl-3-cis,trans-(2',2'-dichlorovinyl)-cyclopropane-1-carboxylic acid as a colorless transparent oil.

Boiling point: 100° C.-110° C./0.4 mmHg
Refractive index: 1.5117 (21° C.)
Yield: 94.0%

STAGE IV-1 EXAMPLE 2

To 80 ml of methanol solution containing 0.92 g of metallic sodium were added 7.8 g of methyl 2,2-dimethyl-3-(2',2',2'-trichloroethyl)-cyclopropanecarboxylate (purity: 87.8%, cis/trans ratio: 88/12) to heat the resulting mixture for 35 hours under reflux. After distilling off the methanol, the mixture was diluted with water, acidified with diluted hydrochloric acid, subjected to extraction with ether. After washing the ether layer with sodium bicarbonate aqueous solution and a saturated sodium chloride aqueous solution, the ether was distilled off. Vacuum distillation was carried out to obtain 5.4 g of methyl 2,2-dimethyl-3-(2',2'-dichlorovinyl)-cyclopropanecarboxylate, b.p. 64°-72° C./1.2 mmHg, cis/trans ratio 90.9/9.1, purity 87.8%, yield 79.8%. Further, the sodium bicarbonate aqueous wash solution was acidified to obtain 0.5 g of 2,2-dimethyl-3-(2',2'-dichlorovinyl)-cyclopropanecarboxylic acid.

STAGE IV-1 EXAMPLE 3

To 120 ml of methanol solution containing 4.8 g of sodium hydroxide were added 11.1 g of 2,2-dimethyl-3-(2',2',2'-trichloroethyl)-cyclopropanecarboxylic acid (purity: 91.8%, cis/trans ratio: 82.8/17.2) to heat the resulting mixture for 37 hours under reflux. The mixture was diluted with water and neutral part was removed by extraction with ether. The water layer was acidified with conc. hydrochloric acid and extracted with ether. The ether layer was concentrated to obtain 8.15 g of 2,2-dimethyl-3-(2',2'-dichlorovinyl)-cyclopropanecarboxylic acid, cis/trans ratio 79.8/20.2, purity 92.4%, yield 86.8%.

STAGE IV-1 EXAMPLE 4

In similar way to that in Stage IV-1 Example 3 above except that 5 g of methyl 2,2-dimethyl-3-(2',2',2'-trichloroethyl)-cyclopropanecarboxylate (purity: 95.8%, cis/trans: 92.7/7.3) were added to a mixture of 4 g of sodium hydroxide, 20 ml of methanol and 30 ml of water to heat the resulting mixture for 10 hours under reflux, 3.31 of 2,2-dimethyl-3-(2',2'-dichlorovinyl)-cyclopropanecarboxylic acid, cis/trans ratio 98.8/1.2, purity 96.4%, yield 81.7% were obtained.

STAGE IV-2 EXAMPLE 1

To a 20-ml eggplant shape flask were added 2.8 g of (±)-1-ethoxycarbonyl-2,2-dimethyl-3-cis,trans-(2',2',2'-trichloroethyl)-cyclopropyl methyl ketone and then 15 g of a 10% aqueous caustic soda solution were added dropwise thereto at room temperature. After refluxing for 3 hours, the reaction mixture was made acidic to pH 1 with a 10% aqueous hydrochloric acid and extracted with 50 ml of benzene. The benzene layer was washed with 20 ml of an aqueous sodium chloride solution and dried over anhydrous magnesium sulfate. After removing the benzene under reduced pressure, vacuum distillation was carried out to obtain 2.1 g of (±)-1-hydroxycarbonyl-2,2-dimethyl-3-cis,trans-(2',2'-dichlorovinyl)-cyclopropyl methyl ketone as a colorless transparent oil.

Boiling point: 135° C.–145° C./0.2 mmHg
Refractive index: 1.5173 (15° C.)
Yield: 86.2%

STAGE II-1→STAGE IV-2 (STAGE II-2) EXAMPLE 1

To 60 ml of a methanol solution containing 2.86 g of sodium hydroxide was added 10 g of 4,4-dimethyl-5,7,7,7-tetrachloroheptane-2-one (purity 97.0%) and stirred at room temperature at first. Gas chromatography analysis showed that 2,2-dimethyl-3-(2',2',2'-trichloroethyl)-cyclopropyl methyl ketone was produced immediately and the cis/trans ratio was 83.3/16.7 at after 2 hours from the start of the reaction and 77.5/22.5 at after 4 hours from the same. Thereafter the reaction mixture was heated, then the cis/trans ratio was changed and together with the increase of the trans isomer, there increased 2,2-dimethyl-3-(2',2'-dichlorovinyl)-cyclopropyl methyl ketone which is the product of dehydrohalogenation reaction. After the reaction mixture was refluxed for 6 hours further 0.3 g of sodium hydroxide was added thereto and the reflux was continued for 8 hours, then it was observed by gas chromatography analysis that the yield of 2,2-dimethyl-3-(2',2'-dichlorovinyl)-cyclopropyl methyl ketone was 93.9% (cis/trans ratio 11.9/88.1) and that of 2,2-dimethyl-3-(2',2',2'-trichloroethyl)-cyclopropyl methyl ketone was 5.1% (cis/trans ratio 0/100).

STAGE III-1→STAGE IV-1 EXAMPLE 1

To 250 ml of methanol solution containing 24 g of sodium hydroxide were added 17 g of 2,2-dimethyl-3-(2',2',2'-trichloroethyl)-cyclopropyl methyl ketone (purity: 97.9%, cis/trans ratio 91.5/8.5) under cooling with ice, and then 40 g of bromine were added dropwise at −10° C. to −5° C. for 20 minutes and after stirring the mixture at the same temperature for 2 hours, 25.2 g of sodium sulfite (7 hydrate) and 250 ml of water were added thereto, and the mixture was heated up to 70° C. and stirred for 47 hours with heating. Then the methanol was distilled off, water was added to the reaction mixture and neutral part was removed by extraction with ether. The water layer was acidified with conc. hydrochloric acid under cooling with ice. The deposited crystals were filtered, washed with water and dried to obtain 9.85 g of 2,2-dimethyl-3-(2',2'-dichlorovinyl)-cyclopropanecarboxylic acid, cis/trans ratio 89.8/10.2, purity 91.8%, yield 72.9%.

What we claim is:

1. A process for producing a cis-rich β-dihalogenoethenylcyclopropane derivative of the formula (VI),

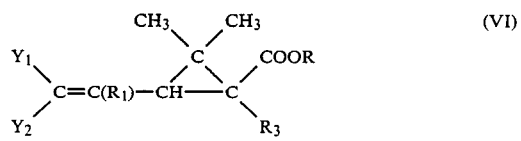

wherein $R_1$ is a hydrogen atom or an alkyl group, $R_3$ is a hydrogen atom and R is a hydrogen atom and each of $Y_1$ and $Y_2$ is a fluorine, chlorine or bromine atom respectively, which comprises a series of sequential steps of reacting an alkyl 3-butenyl ketone derivative of the formula (I)

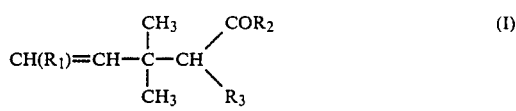

wherein $R_1$ is a hydrogen atom or an alkyl group, $R_2$ is a methyl group and $R_3$ is a hydrogen atom, with a tetrahalogenomethane of the formula,

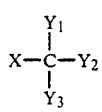

wherein X is a chlorine or bromine atom and each of $Y_1$, $Y_2$ and $Y_3$ is a fluorine, chlorine or bromine atom respectively, provided that when X is a chlorine atom each of $Y_1$, $Y_2$ and $Y_3$ is a fluorine or chlorine atom, in an organic solvent selected from the group consisting of t-butyl alcohol, t-amyl alcohol, isopropyl alcohol, acetonitrile, dimethyl formamide and dimethyl sulfoxide, at a temperature of from 30°–200° C., in the presence of a catalyst comprising a combination of cuprous, cupric, ferrous and ferric salts, and at least one member selected from monoethanolamine, diethanolamine and triethanolamine, to form an alkyl 3,5,5,5-tetrahalogenopentyl ketone derivative of the formula (II),

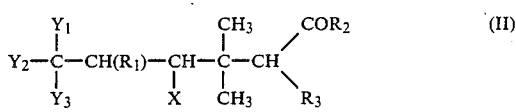

wherein $R_1$, $R_2$, $R_3$, X, $Y_1$, $Y_2$ and $Y_3$ are as defined above, reacting at a temperature of from $-20°$ to $25°$ the resulting alkyl 3,5,5,5-tetrahalogenopentyl ketone derivative of the formula (II) with an alkali metal hydroxide in water or in a mixture of water and alcohol selected from the group consisting of methanol, ethanol, propanol and butanol to form a cis-rich alkyl cyclopropyl ketone derivative of the formula (III),

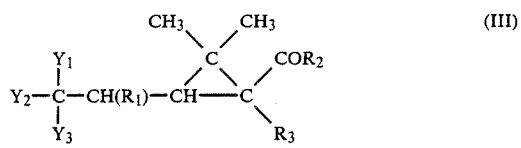

wherein $R_1$, $R_2$, $Y_1$, $Y_2$ and $Y_3$ are as defined above and $R_3$ is a hydrogen atom, oxidizing the resulting alkyl cyclopropyl ketone derivative of the formula (III) with a haloform reagent of the formula

MOX' wherein M is sodium, potassium or calcium and X' is chlorine, bromine or iodine, or by introducing a halogen in the presence of a lower alcohol into an aqueous alkali metal hydroxide solution of the derivative of formula (III) to form a cis-rich cyclopropane-carboxylic acid derivative of the formula (V)

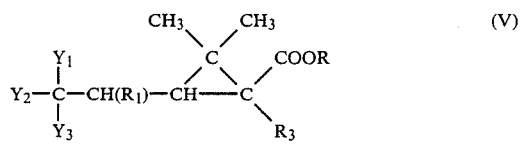

wherein $R_1$, $R_3$, $Y_1$, $Y_2$ and $Y_3$ are as defied above and R is a hydrogen atom or a lower alkyl group, and then reacting the resulting β-trihalogenoethylcyclopropanecarboxylic acid derivative of the formula (V) with sodium hydroxide, potassium hydroxide or calcium hydroxide in water, an organic alcohol or a mixture thereof to form a cis-rich β-dihalogenoethenylcyclopropanecarboxylic acid derivative of the formula (VI).

2. A process for producing a transrich β-dihalogenoethenylcyclopropane derivative of the formula (VI),

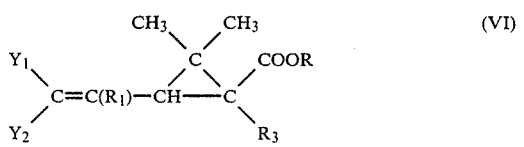

wherein $R_1$ is a hydrogen atom or an alkyl group, $R_3$ is a hydrogen atom and R is a hydrogen atom or a lower alkyl group and each of $Y_1$ and $Y_2$ is a fluorine, chlorine or bromine atom respectively, which comprises a series of sequential steps of reacting an alkyl 3-butenyl ketone derivative of the formula (I)

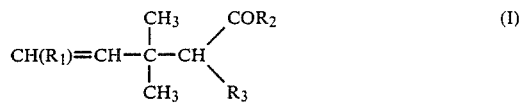

wherein $R_1$ is a hydrogen atom or an alkyl group, $R_2$ is a methyl group and $R_3$ is a hydrogen atom, with a tetrahalogenomethane of the formula,

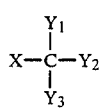

wherein X is a chlorine or bromine atom and each of $Y_1$, $Y_2$ and $Y_3$ is a fluorine, chlorine or bromine atom respectively, provided that when X is a chlorine atom each of $Y_1$, $Y_2$ and $Y_3$ is a fluorine or chlorine atom, in an organic solvent selected from the group consisting of t-butyl alcohol, t-amyl alcohol, isopropyl alcohol, acetonitrile, dimethyl formamide and dimethyl sulfoxide, at a temperature of from 30°–200° C., in the presence of a catalyst comprising a combination of cuprous, cupric, ferrous and ferric salts, and at least one member selected from monoethanolamine, diethanolamine and triethanolamine, to form an alkyl 3,5,5,5,-tetrahalogenopentyl ketone derivative of the formula (II),

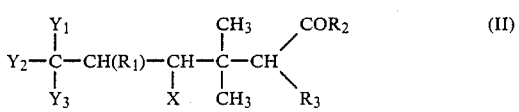

wherein $R_1$, $R_2$, $R_3$, X, $Y_1$, $Y_2$ and $Y_3$ are as defined above, reacting at a temperature of from above 25° C. to 120° C. the resulting alkyl 3,5,5,5-tetrahalogenopentyl ketone derivative of the formula (II) with an alkali metal hydroxide in water or in a mixture of water and an alcohol selected from the group consisting of methanol, ethanol, propanol and butanol under a severe condition to form a trans-rich β-dihalogenoethenylcyclopropyl ketone derivative of the formula (IV),

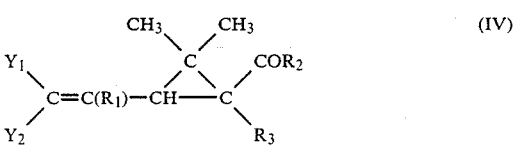

wherein $R_1$, $R_2$, $R_3$, $Y_1$, and $Y_2$ are as defined above, and then oxidizing the resulting trans-rich β-dihalogenoethenylcyclopropyl ketone derivative of the formula (IV) at a temperature of from $-20°$ to $70°$ C. with a haloform reagent of the formula

MOX' where M is sodium, potassium or calcium and X' is chlorine, bromine or iodine, or by introducing a halogen in the presence of a lower alcohol into an aqueous alkali metal hydroxide solution of the derivative of formula (IV) to form a trans-rich β-dihalogenoethyenylcyclopropanecarboxylic acid derivative of the formula (VI).

3. A process for producing a cis-rich alkyl cyclopropyl ketone derivative of the formula (III),

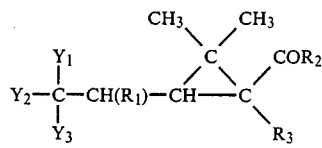 (III)

wherein $R_1$ is a hydrogen atom or an alkyl group, $R_2$ is a methyl group and $R_3$ is a hydrogen atom and each of $Y_1$, $Y_2$ and $Y_3$ is a fluorine, chlorine or bromine, respectively, atom which comprises reacting at a temperature of from $-20°$ to $25°$ C. a 3,5,5,5-tetrahalogenopentyl ketone derivative of the formula (II),

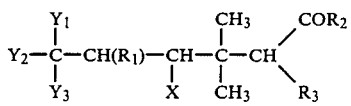 (II)

wherein $R_1$ is a hydrogen atom or an alkyl group, $R_2$ is a methyl group and $R_3$ is a hydrogen atom, X is a chlorine or bromine atom and each of $Y_1$, $Y_2$ and $Y_3$ is a fluorine, chlorine or bromine atom respectively, provided that when X is a chlorine atom each of $Y_1$, $Y_2$ and $Y_3$ is a fluorine or chlorine atom, with an alkali metal hydroxide in water or in methanol, ethanol, a propanol and a butanol with water to form a cis-rich alkyl cyclopropyl ketone derivative of the formula (III).

4. The process for producing cis-rich (±)-2,2-dimethyl-3-(2',2'-dichlorovinyl)-cyclopropane-1-carboxylic acid of the formula,

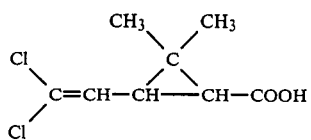

which comprises a series of sequential steps of
(1) reacting 4,4-dimethyl-5-hexene-2-one of the formula,

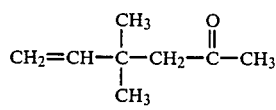

with a carbon tetrachloride, in an organic solvent selected from the group consisting of t-butyl alcohol, t-amyl alcohol, isopropyl alcohol, acetonitrile, dimethyl formamide and dimethyl sulfoxide at a temperature of from 30°-200° C. in the presence of a catalyst comprising a combination of cuprous, cupric, ferrous and ferric salts, and at least one member selected from monoethanolamine, diethanolamine and triethanolamine, to form 4,4-dimethyl-5,7,7,7-tetrachloroheptane-2-one of the formula,

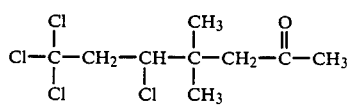

(2) reacting at a temperature of from $-20°$ to $25°$ C. the resultant 4,4-dimethyl-5,7,7,7-tetrachloroheptane-2-one with sodium hydroxide in water to form cis-rich 2,2-dimethyl-3-(2',2',2'-trichloroethyl)-cyclopropyl methyl ketone of the formula,

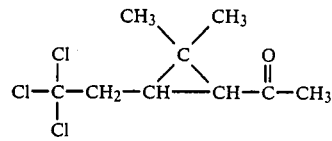

(3) reacting the resultant cis-rich 2,2-dimethyl-3-(2',2',2'-trichloroethyl)-cyclopropyl methyl ketone at a temperature of from $-20°$ to $70°$ C. with sodium hypochlorite to form cis-rich (±)-2,2-dimethyl-3-(2',2',2'-trichloroethyl)-cyclopropane-1-carboxylic acid of the formula,

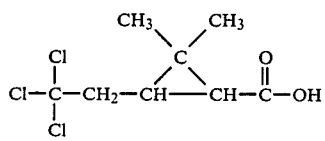

(4) reacting the resultant cis-rich (±)-2,2,2,-dimethyl-3-(2',2',2'-trichloroethyl)-cyclopropane-1-carboxylic acid with sodium hydroxide in water to form cis-rich (±)-2,2-dimethyl-3-(2'2'-dichlorovinyl)-cyclopropane-1-carboxylic acid.

5. The process for producing trans-rich (±)-2,2-dimethyl-3-(2',2'-dichlorovinyl)-cyclopropane-1-carboxylic acid of the formula,

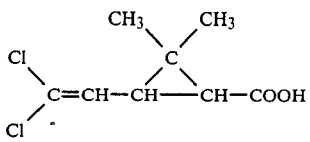

which comprises a series of sequential steps of
(1) reacting 4,4-dimethyl-5-hexane-2-one of the formula,

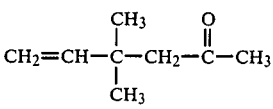

with carbon tetrachloride, in an organic solvent selected from the group consisting of t-butyl alcohol, t-amyl alcohol, isopropyl alcohol, acetonitrile, dimethyl formamide and dimethyl sulfoxide, at a temperature of from 30°-200° C. in the presence of a catalyst comprising a combination of cuprous, cupric, ferrous and ferric salts, and at least one member selected from monoethanolamine, diethanolamine and triethanolamine, to form 4,4-dimethyl-5,7,7,7-tetrachloroheptane-2-one of the formula

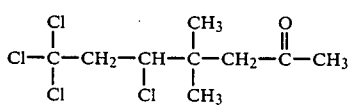

(2) reacting at a temperature of from above $-25°$ C. to 120° C. the resultant 4,4-dimethyl-5,7,7,7-tetrachloroheptane-2-one with sodium hydroxide in water under severe condition to form trans-rich (±)-2,2-dimethyl-3-(2',2'-dichlorovinyl)-cyclopropyl methyl ketone of the formula,

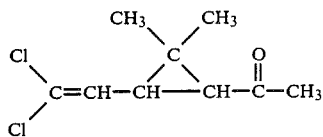

(3) reacting the resultant trans-rich (±)-2,2-dimethyl-3-(2',2'-dichlorovinyl)-cyclopropyl methyl ketone with sodium hypochlorite at a temperature of −20° to 70° C. to form trans-rich (±)-2,2-dimethyl-3-(2',2'-dichlorovinyl)-cyclopropane-2-carboxylic acid.

6. A process for producing a cis-rich alkyl cyclopropyl ketone deriavtive of the formula (III),

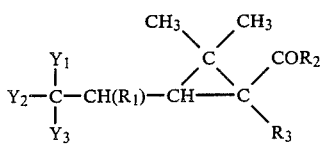

wherein $R_1$ is a hydrogen atom or an alkyl group, $R_2$ is a methyl group, $R_3$ is a hydrogen atom, and each of $Y_1$, $Y_2$ and $Y_3$ is a fluorine, chlorine or bromine atom respectively, which comprises a series of sequential steps of reacting an alkyl 3-butenyl ketone derivative of the formula (I)

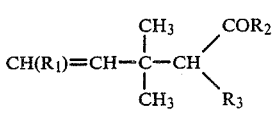

wherein $R_1$ $R_2$ and $R_3$ are as defined above, with a tetrahalogenomethane of the formula,

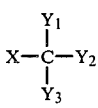

wherein X is a chlorine or bromine atom and each of $Y_1$, $Y_2$ and $Y_3$ is a fluorine, chlorine or bromine atom respectively, provided that when X is a chlorine atom each of $Y_1$, $Y_2$ and $Y_3$ is a fluorine or chlorine atom, in an organic solvent selected from the group consisting of t-butyl alcohol, t-amyl alcohol, isopropyl alcohol, acetonitrile, dimethyl formamide and dimethyl sulfoxide at a temperature of from 30°–200° C. in the presence of a catalyst comprising a combination of cuprous, cupric, ferrous and ferric salts, and at least one member selected from monoethanolamine, diethanolamine and triethanolamine, to form an alkyl 3,5,5,5-tetrahalogenopentyl ketone derivative of the formula (II),

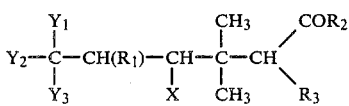

wherein $R_1$, $R_2$, $R_3$, X, $Y_1$, $Y_2$ and $Y_3$ are as defined above, and reacting at a temperature of from −20° to 25° C. the resulting alkyl 3,5,5,5-tetrahalogenopentyl ketone derivative of the formula (II) with an alkali metal hydroxide in water or in a mixture of water and an alcohol selected from the group consisting of methanol, ethanol, propanol and butanol to form a cis-rich alkyl cyclpropyl ketone derivative of the formula (III).

7. A process of producing a trans-rich β-dihalogenoethenylcyclopropyl ketone derivative of the formula (IV),

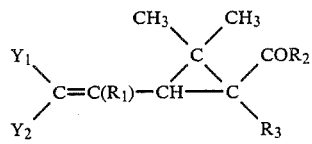

wherein $R_1$ is a hydrogen atom or an alkyl group, $R_2$ is a methyl group and $R_3$ is a hydrogen atom and each of $Y_1$ and $Y_2$ is a fluorine, chlorine, or bromine atom, respectively, which comprises a series of sequential steps of reacting an alkyl 3-butenyl ketone derivative of the formula (I)

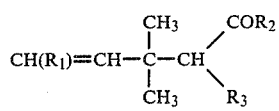

wherein $R_1$, $R_2$ and $R_3$ are as defined above, with a tetrahalogenomethane of the formula,

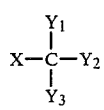

wherein X is a chlorine or bromine atom of each of $Y_1$, $Y_2$ and $Y_3$ is a fluorine, chlorine or bromine atom, respectively, provided that when X is a chlorine atom each of $Y_1$, $Y_2$ and $Y_3$ is a fluorine or chlorine atom, in an organic solvent selected from the group consisting of t-butyl alcohol, t-amyl alcohol, isopropyl alcohol, acentonitrile, dimethyl formamide or dimethyl sulfoxide, at a temperature of 30°-200° C., in the presence of a catalyst comprising a combination of cuprous, cupric, ferrous and ferric salts, and at least one member selected from monaethanolamine, diethanolamine and triethanolamine to form an alkyl 3,5,5,5-tetrahalogenopentyl ketone derivative of the formula (II)

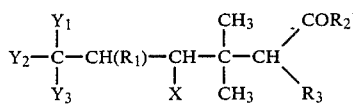

wherein $R_1$, $R_2$, $R_3$, X, $Y_1$, $Y_2$ and $Y_3$ are as defined above and reacting at a temperature of from above 25° C. to 120° C. the resulting alkyl 3,5,5,5-tetrahalogenopentyl ketone derivative of the formula (II) with an alkali metal hydroxide in water or in methanol, ethanol, a propanol, a butanol or mixtures thereof with water under a severe condition to form a trans-rich 62-dihalogenoethenylcyclopropyl ketone derivative of the formula (IV).

8. A process for producing a cis-rich cyclopropanecarboxylic acid derivative of the formula (V),

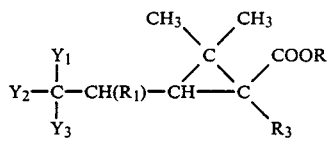 (V)

wherein $R_1$ is a hydrogen atom or an alkyl group, $R_3$ is a hydrogen atom and R is a hydrogen atom or a lower alkyl group and each of $Y_1$, $Y_2$ and $Y_3$ is a fluorine, chlorine or bromine atom respectively, which comprises a series of sequential steps of reacting an alkyl 3-butenyl ketone derivative of the formula (I)

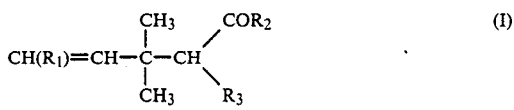 (I)

wherein $R_1$ is a hydrogen atom or an alkyl group, $R_2$ is a methyl group and $R_3$ is a hydrogen atom, with a tetrahalogenomethane of the formula,

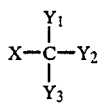

wherein X is a chlorine or bromine atom and each of $Y_1$, $Y_2$ and $Y_3$ is a fluorine, chlorine or bromine atom respectively, provided that when X is a chlorine atom each of $Y_1$, $Y_2$ and $Y_3$ is a fluorine or chlorine atom, in an organic solvent selected from the group consisting of t-butyl alcohol, t-amyl alcohol, isopropyl alcohol, acetonitrile, dimethyl formamide and dimethyl sulfoxide, at a temperature of from 30°–200° C., in the presence of a catalyst comprising a combination of cuprous, cupric, ferrous and ferric salts, and at least one member selected from monoethanolamine, diethanolamine and triethanolamine to form an alkyl 3,5,5,5-tetrahalogenopentyl ketone derivative of the formula (II),

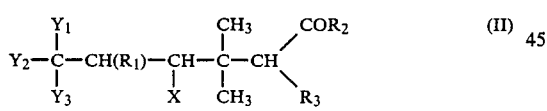 (II)

wherein $R_1$, $R_2$, $R_3$, X, $Y_1$, $Y_2$ and $Y_3$ are as defined above and reacting at a temperature of from −20° to 25° C. the resulting alkyl 3,5,5,5-tetrahalogenopentyl ketone derivative of the formula (II) with an alkali metal hydroxide in water or in a mixture of water and an alcohol selected from the group consisting of methanol, ethanol, propanol and butanol to form a cis-rich alkyl cyclopropyl ketone derivative of the formula (III),

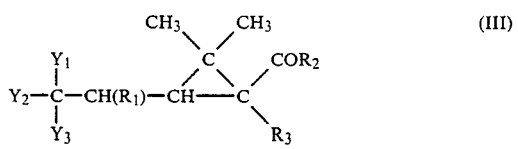 (III)

wherein $R_1$, $R_2$, X, $Y_1$, $Y_2$ and $Y_3$ are as defined above and $R_3$ is a hydrogen atom and oxidizing at a temperature of −20°–70° C. the resulting cis-rich alkyl cyclopropyl ketone derivative of the formula (III) with a haloform reagent of the formula

MOX' wherein M is sodium, potassium or calcium and X' is chlorine, bromine or iodine, or by introducing a halogen in the presence of a lower alcohol into an aqueous alkali metal hydroxide solution of a cis-rich derivative of the formula (III) to form a cyclopropanecarboxylic acid derivative of the formula (V).

9. A process for producing a cyclopropane carboxylic acid derivative of the formula (V),

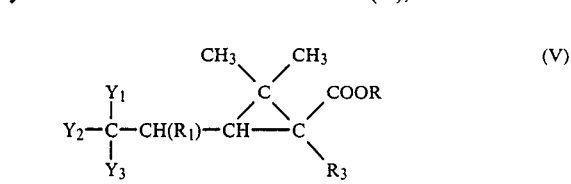 (V)

wherein $R_1$ is a hydrogen atom or an alkyl group, $R_3$ is a hydrogen atom and R is a hydrogen atom or a lower alkyl group and each of $Y_1$, $Y_2$ and $Y_3$ is a fluorine, chlorine or bromine atom respectively, which comprises a series of sequential steps of reacting an alkyl 3,5,5,5-tetrahalogenopentyl ketone derivative of the formula (II),

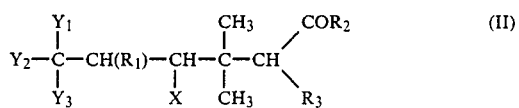 (II)

wherein $R_1$, $R_3$, X, $Y_1$, $Y_2$ and $Y_3$ are as defined above and $R_2$ is a methyl group at a temperature of from −20° to 25° C. with an alkali metal hydroxide in water or in a mixture of water and an alcohol selected from the group consisting of methanol, ethanol, propanol and butanol to form a cis-rich alkyl cyclopropyl ketone derivative of the formula (III),

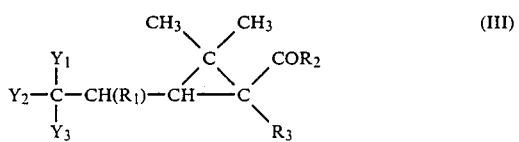 (III)

wherein $R_1$, $R_2$, $R_3$, $Y_1$, $Y_2$ and $Y_3$ are as defined above, and oxidizing the resulting cis-rich alkyl cyclopropyl ketone derivative of the formula (III) with a haloform reagent of the formula

MOX' wherein M is sodium, potassium or calcium and X' is chlorine, bromine or iodine, or by introducing a halogen in the presence of a lower alcohol into an aqueous alkali metal hydroxide solution of a cis-rich derivative of the formula (III) to form a cyclopropanecarboxylic acid derivative of the formula (V).

10. A process for producing a trans-rich β-dihalogenoethenylcyclopropane derivative of the formula (VI),

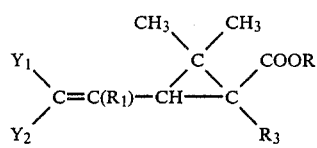
(VI)

wherein $R_1$ is a hydrogen atom or an alkyl group, $R_2$ is a methyl group, $R_3$ is a hydrogen atom and R is a hydrogen atom and each of $Y_1$ and $Y_2$ is a fluorine, chlorine, or bromine atom, respectively, which comprises a series of sequential steps of reacting an alkyl 3,5,5,5-tetrahalogenopentyl ketone derivative of the formula (II),

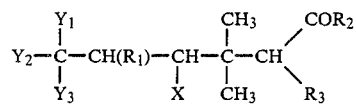
(II)

wherein $R_1$, $R_2$ and $R_3$ are as defined above, X is a chlorine or bromine atom and each of $Y_1$, $Y_2$ and $Y_3$ is a fluorine, chlorine or bromine atom, respectively, provided that when X is a chlorine atom each of $Y_1$, $Y_2$ and $Y_3$ is a fluorine or chlorine atom, at a temperature of from above 25° C. to 120° C. with an alkali metal hydroxide in water, or in a mixture of water and an alcohol selected from the group consisting of methanol, ethanol, propanol and butanol under a severe condition to form a trans-rich β-dihalogenoethenylcyclopropyl ketone derivative of the formula (IV),

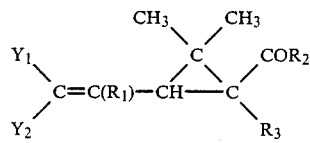
(IV)

wherein $R_1$, $R_2$, $R_3$, $Y_1$, and $Y_2$ are as defined above, and then oxidizing the resulting trans-rich β-dihalogenoethenycyclopropyl ketone derivative of the formula (IV) at a temperature of from −20°–70° C. with a haloform reagent of the formula

MOX′ wherein M is sodium, potassium or calcium and X′ is chlorine, bromine or iodine or by introducing a halogen in the presence of a lower alcohol into an aqueous alkali metal hydroxide solution of a trans-rich derivative of the formula (IV), to form a trans-rich β-dihalogenoethenyleyclopropanecarboxylic acid derivative of the formula (VI).

11. A process for producing a cis-rich β-dihalogenoethenylcyclopropane derivative of the formula (VI),

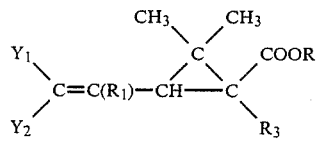
(VI)

wherein $R_1$ is a hydrogen atom or an alkyl group, $R_3$ is a hydrogen atom and R is a hydrogen atom or a lower alkyl group and each of $Y_1$ and $Y_2$ is a fluorine, chlorine or bromine atom respectively, which comprises a series of sequential steps of reacting an alkyl 3,5,5,5-tetrahalogenopentyl ketone derivative of the formula (II)

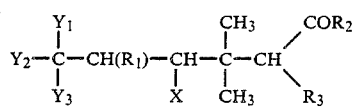
(II)

wherein $R_1$, $R_3$, X, $Y_1$, $Y_2$ and $Y_3$ are as defined above and $R_2$ is a methyl group at a temperature of from −20° to 25° C. with an alkali metal hydroxide in water or in a mixture of water and an alcohol selected from the group consisting of methanol, ethanol, propanol and butanol to form a cis-rich alkyl cyclopropyl ketone derivative of the formula (III),

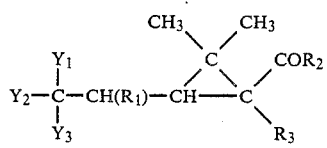
(III)

wherein $R_1$, $R_2$, $R_3$, $Y_1$, $Y_2$ and $Y_3$ are as defined above, oxidizing at a temperature of −20°–70° C. the resulting cis-rich alkyl cyclopropyl ketone derivative of the formula (III) with a haloform reagent of the formula

MOX′ wherein M is sodium, potassium or calcium and X′ is chlorine, bromine or iodine or by introducing a halogen in the presence of a lower alcohol into an aqueous alkali metal hydroxide solution a cis-rich derivative of the formula (III) to form a cyclopropanecarboxylic acid derivative of the formula (V),

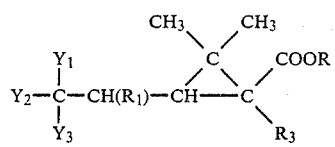
(V)

wherein $R_1$, $R_3$, R, $Y_1$, $Y_2$ and $Y_3$ are as defined above, and then reacting the resulting β-trihalogenoethylcyclopropanecarboxylic acid derivative of the formula (V) with sodium hydroxide, potassium hydroxide or calcium hydroxide in water, an organic alcohol or a mixture thereof to form a β-dihalogenoethenylcyclopropanecarboxylic acid derivative of the formula (VI) wherein formulas (V) and (VI) each define a cis-rich compound.

12. A process for producing a trans alkylcyclopropyl ketone derivative of the formula (IV),

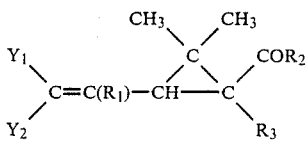
(IV)

wherein $R_1$ is a hydrogen atom or an alkyl group, $R_2$ is a methyl group, $R_3$ is a hydrogen atom, and each of $Y_1$ and $Y_2$ is a fluorine, chlorine, or bromine atom, respectively, which comprises reacting at a temperature of from higher than 25° C. to 120° C. 3,5,5,5-tetrahalogenopentyl ketone derivative of the formula (II),

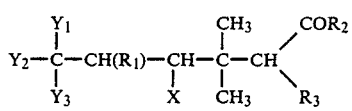

wherein $R_1$, $R_2$ and $R_3$ are as defined above, X is a chlorine or bromine atom and each of $Y_1$, $Y_2$ and $Y_3$ is a fluorine, chlorine or bromine atom, respectively, provided that when X is a chlorine atom, each of $Y_1$, $Y_2$ and $Y_3$ is a fluorine or chlorine atom, with an alkali metal hydroxide in water or in a mixture of water and an alcohol selected from the group consisting of methanol, ethanol, propanol and butanol to form a trans-rich alkyl cyclopropyl ketone derivative of the formula (IV).

* * * * *